(12) United States Patent
Chung et al.

(10) Patent No.: US 6,280,753 B1
(45) Date of Patent: Aug. 28, 2001

(54) WATER CONTAINING WAX-BASED PRODUCT

(75) Inventors: Kenny Chung, Dix Hills; Tracy N. Keeler, East Northport; Manuel L. Tan, Westbury, all of NY (US)

(73) Assignee: E-L Management Corporation, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/424,463

(22) PCT Filed: May 27, 1998

(86) PCT No.: PCT/US98/10725

§ 371 Date: Feb. 25, 2000

§ 102(e) Date: Feb. 25, 2000

(87) PCT Pub. No.: WO98/53793

PCT Pub. Date: Dec. 3, 1998

Related U.S. Application Data

(63) Continuation-in-part of application No. 08/864,162, filed on May 28, 1997, now Pat. No. 6,039,960.

(51) Int. Cl.[7] .............................. A61K 6/00; A61K 7/00; A61K 7/025; A61K 9/66; A61K 9/127
(52) U.S. Cl. .......................... 424/401; 64/450; 64/451; 64/455
(58) Field of Search .................. 424/64, 450, 451, 424/455, 407

(56) References Cited

U.S. PATENT DOCUMENTS

| | | | |
|---|---|---|---|
| 4,855,090 | 8/1989 | Wallach | 264/4.1 |
| 4,895,452 | 1/1990 | Yiournas et al. | 366/173 |
| 4,911,928 | 3/1990 | Wallach | 424/450 |
| 4,917,951 | 4/1990 | Wallach | 428/402.2 |
| 4,942,038 | 7/1990 | Wallach | 424/450 |
| 5,000,960 | 3/1991 | Wallach | 424/450 |
| 5,013,497 | 5/1991 | Yiournas et al. | 264/4.1 |
| 5,015,469 | 5/1991 | Yoneyama et al. | 424/59 |
| 5,023,086 | 6/1991 | Wallach | 424/450 |
| 5,032,457 | 7/1991 | Wallach | 428/402.2 |
| 5,104,736 | 4/1992 | Wallach | 428/402.2 |
| 5,108,737 | 4/1992 | Dunphy et al. | 424/64 |
| 5,147,723 | 9/1992 | Wallach | 428/402.2 |
| 5,160,669 | 11/1992 | Wallach et al. | 264/4.3 |
| 5,213,805 | 5/1993 | Wallach et al. | 424/450 |
| 5,219,538 | 6/1993 | Henderson et al. | 428/402.2 |
| 5,234,767 | 8/1993 | Wallach | 428/402.2 |
| 5,256,422 | 10/1993 | Albert et al. | 424/450 |
| 5,260,065 | 11/1993 | Nashua et al. | 424/450 |
| 5,342,134 | 8/1994 | Lombardi et al. | 401/78 |
| 5,405,615 | 4/1995 | Mathur | 424/450 |
| 5,439,967 | 8/1995 | Mathur | 424/450 |
| 5,474,848 | 12/1995 | Wallach | 428/402.2 |
| 5,560,917 | 10/1996 | Cohen et al. | 424/401 |
| 5,756,014 | 5/1998 | Mathur | 264/4.1 |
| 6,039,960 | * 3/2000 | Chung et al. | 424/401 |

FOREIGN PATENT DOCUMENTS

| | | | |
|---|---|---|---|
| 0 522 624 A1 | 1/1993 | (EP) | A61K/7/27 |
| WO 94/06400 | 3/1994 | (WO) | A61K/7/00 |

\* cited by examiner

*Primary Examiner*—Thurman K. Page
*Assistant Examiner*—S. Howard
(74) *Attorney, Agent, or Firm*—Pennie & Edmonds L

(57) ABSTRACT

The present invention relates to a wax-based composition comprising at least about 0.5–30% water in a water-in-oil emulsion, wherein water is encapsulated in a lamellar lipid vesicle capable of withstanding wax melting point temperatures. The composition is useful in delivering water soluble actives in an anhydrous base, and is particularly well-adapted for uses in lipsticks and lip-care products.

31 Claims, No Drawings

WATER CONTAINING WAX-BASED PRODUCT

RELATED APPLICATIONS

This application is a continuation-in-part of U.S. Ser. No. 08/864,162, filed May 28, 1997, now U.S. Pat. No. 6,039,960, the contents of which is incorporated by reference herein in its entirety.

FIELD OF THE INVENTION

The present invention relates to cosmetic and/or therapeutic products. In particular, the invention relates to wax-based products containing water in the formulation.

BACKGROUND OF THE INVENTION

In recent years, lipstick has gone beyond the point of serving the sole function of coloring the lips. Consumers are no longer satisfied with a product which serves a simple cosmetic purpose; rather, the demand is now for a product which, in addition to providing an attractive appearance, goes on smoothly, lasts all day, and also moisturizes and improves the condition of the lips. The goals of moisturizing and conditioning have proven particularly difficult when using standard lipstick formulations.

Traditional lipsticks have primarily been anhydrous, i.e., they have been composed principally of hydrophobic waxes and oils. Such products have relied on the formation of a thick occlusive film on the lips to prevent moisture loss. While to a large extent very effective in preventing water loss, such anhydrous systems are unable to achieve the more desirable end of actively reconstituting the lips' lipid barrier or attracting and binding water to the lip surface. This is largely because the low polarity and high viscosity which characterize the typical waxy components, act as a barrier to active product diffusion. Moreover, these viscous materials frequently result in a product that leaves an undesirable greasy or waxy feeling on the lips.

Notwithstanding the problems which arise with their use, the hydrophobic waxes and oils are an essential part of virtually any lipstick, in that they confer the solid physical structure required for ease of application. It has been recognized that the availability of a water-containing lip product would obviate many of the problems associated with the anhydrous systems. For example, many of the therapeutic or conditioning actives which would be useful in barrier repair or moisture attraction are water soluble. ideally, the use of a water-in-oil emulsion system would provide the combination of features which would both confer both occlusive film-forming properties and structural integrity to the stick while still permitting delivery of the water soluble and/or water attracting actives to the lips. Nonetheless, the cosmetics industry has, to date, produced few such systems. In part, the difficulty arises in the inherent incompatibility of water with the low polarity waxes and oils; however, there are also serious problems with loss of water from the stick during storage, and the lack of stability of the water soluble actives in such a system. Generally speaking, the available systems rely entirely on the use of emulsifiers (see e.g., U.S. Pat. No. 5,342,134) to stabilize the contained actives. Since the trend in cosmetics is away from the use of emulsifiers, however, it would be preferable to design a water-in-oil emulsion system which does not rely solely on standard emulsifiers for stability of actives contained therein.

Therefore, there continues to be a need for a water-containing lip product which can moisturize and protect the lips, deliver stable water soluble actives without the use of large amounts of standard emulsifiers or surfactants, and which is not susceptible to rapid loss of water from the mass. The present invention provides such a product, and solves many of the problems encountered with other water-containing lip products.

SUMMARY OF THE INVENTION

The present invention relates to a wax-based composition comprising at least about 0.5–30% water in a water-in-oil emulsion, wherein water is encapsulated in a lamellar lipid vesicle capable of withstanding the temperatures encountered in a hot-pour process, i.e., wax or wax-like materials' melting point temperatures. By "wax-based" is meant a product which contains over 5% by weight, more preferably over 10%, of wax or a wax-like product in the formulation. The vesicle preferably has walls comprising at least one high melting point polyoxyethylene fatty acid ether, which confers the high temperature stability required for pouring lipstick or other wax-based products. The products so prepared lose water at a slower rate than other water-containing lip products, and are capable of maintaining the stability of water soluble actives contained within the vesicle. In a preferred embodiment, the wax base is designed to contain several products with a relatively moderate to high level of polarity, so as to enhance compatibility with the water-containing vesicle.

DETAILED DESCRIPTION OF THE INVENTION

The use of lamellar vesicles to encapsulate and deliver both cosmetic and pharmaceutical actives has now long been established. In brief, these vesicles comprise one or more lipid layers, each surrounding a small aqueous volume. Such vesicles and methods of making same have been described in, for example, U.S. Pat. Nos. 4,895,452, 4,855,090, 4,911,928, 4,917,951, 4,942,038, 5,000,960, 5,013,497, 5,023,086, 5,032,457, 5,104,736, 5,147,723, 5,160,669, 5,213,805, 5,219,538, 5,234,767, 5,256,422, 5,260,065, 5,405,615, 5,439,967, and 5,474,848. The contents of each of these is incorporated by reference in its entirety. This type of vesicle is widely recognized as facilitating delivery of a number of different types of actives to a desired target site. A particularly useful type of lamellar vesicle for the present purpose is one which is primarily non-phospholipid in nature. Such vesicles can be made from a wide variety of different components, as can be readily discerned from the cited references. A typical example of the components of an appropriate vesicle are, for example, a sterol, such as cholesterol; one or more surfactants (for example, fatty acids, fatty alcohols, and ethoxylated derivatives thereof, or sorbitan derivatives), and other oils or lipids. However, such vesicles have not previously been used in lipsticks, as the most commonly used components of the vesicle wall typically have a temperature stability maximum of about 50° C.; therefore, the vesicles cannot withstand the high temperature required in the preparation of lipsticks, or other hot-pour products.

It has now been determined that the use of an polyoxyethylene fatty ethers having a melting point greater than that of the waxes being used is adequate to stabilize the other more heat labile components of the vesicle. Preferably, the combined wall materials, including the ether, overall have a melting point at least 2° C. above that of the waxes or wax-type products being used in the hot-pour. Using a lipstick as an exemplary wax-based product, the melting point of the ether is preferably at least about 80° C., preferably at least about 90° C., and more preferably at least about 100° C. The ether is present in an amount of from about 0.01–8%, preferably from about 0.1–5%, and more preferably form about 0.5–4%. Preferred compounds of this type include long chain (i.e., at least C20) polyethylene glycol ethers of a mixture of fatty alcohols with an average of at least 3 moles of ethylene oxide. Particularly preferred are such alcohols having a chain length of at least C40, and an average of 3 moles of ethylene oxide, for example, C40–C60 pareth-3.

The remaining components of the vesicle can be any of those which are standard in the art, as noted above. In particular, vesicle components are described in detail in the U.S. Patent documents listed above, which are incorporated by reference herein. In a preferred embodiment, the lipid layer of the vesicle comprises, in addition to the high melting point ether, a least one other standard polyoxyethylene fatty acid ether, for example polyoxyethylene (n) cetyl, stearyl, oleyl, or linoleyl ethers, wherein the average n value can be from 2–10. Other standard surfactants can also be incorporated into the lipid portion. Preferably, the lipid portion also comprises a sorbitan derivative surfactant, for example, polyoxyethylene sorbitan fatty acid esters (TWEEN, ICI). The lipid layer will also comprise a steroid component. This is preferably a sterol, for example cholesterol or any other sterol with similar chemical properties. In a preferred embodiment, the sterol is a phytosterol, for example, soy sterol, or a phytosterol containing material, such as avocadin.

The lipid layer will also contain any other lipophilic material, e.g., lipophilic emollients, which may be useful for the intended end use of the product. Lipophilic actives may be added to the lipid phase of the vesicle, provided they are stable at the high temperatures at which the product is prepared. In preparation of the vesicle, all lipophilic materials are combined into a single lipophilic phase. The aqueous phase is prepared separately, and comprises water, preferably in an amount of from about 0.5–70% of the vesicle mixture as a whole, and any hydrophilic material which is desired to be incorporated into the product as a whole; examples of such include, water soluble preservatives and antioxidants; water soluble actives or skin conditioning agents, for example, humectants, such as hyaluronic acid salts, hydrogels, or glycerol or elastin; collagen; alpha and beta-hydroxy acids; or milk protein. The determination of proportions of the individual components, including actives, of the two phases is readily made by the skilled artisan in accordance with the standard usage in the art. It will be noted that the amounts of each component employed in the vesicle are not especially crucial, and ratios for the components may be varied, as described, for example, in U.S. Pat. Nos. 5,260,065 and 5,256,422. In the final stage of preparation, the individual phases are combined under high shear, using methods well known in the art, to form lamellar lipid vesicles suspended in a continuous aqueous phase, which is then ready for incorporation into the wax base.

The preparation of the lamellar vesicle solves the problem of providing a stable vehicle for water and water soluble actives. However, it is then necessary to incorporate this highly aqueous vehicle into a strongly hydrophobic wax base. As noted above, a water-in-oil emulsion is in principle the preferred vehicle for providing ease of application combined with the necessary moisturizing but non-greasy properties the consumer desires; however, in practice, the preparation of an appealing, effective and stable solid water-in-oil emulsion has been difficult. It has been surprisingly found, however, that a hydrophobic wax base which accommodates a large percentage of water, with the use of a very small amount of emulsifier, can be obtained.

An anhydrous waxy base constitutes the oil component of the water-in-oil emulsion, and typically comprises at least one wax, one oil, and one emulsifier. The anhydrous base constitutes from about from about 70–99.5% of the total wax based product. The wax component of the anhydrous base contains any one or a combination of cosmetically or pharmaceutically acceptable waxes in an amount of from about 10–40% of the total anhydrous base, and greater than 5%, preferably about 10% to about 30% by weight of the total wax-based product. In the context of the present invention, the term "wax" will be understood to encompass any organic component that is solid at room temperature, which component can be used to solidify the liquid components of the product when all are heated together, then cooled to room temperature. This definition includes waxes in the traditional sense, i.e., those plant, animal or mineral waxes containing primarily esters of higher fatty acids and alcohols, free higher acids and alcohols, and saturated hydrocarbons; examples of such traditional waxes include, but are not limited to, carnauba wax, candelilla wax, beeswax, synthetic wax, shellac wax, spermaceti, lanolin wax, ozokerite, bran wax, ceresin wax, bayberry wax, paraffin, rice wax and jojoba wax. However, it also includes other non-traditional wax-like materials, including, but not limited to, various fatty alcohols, fatty acids, fatty esters, polyethylenes, polyethylene glycols, and sterols as well as synthetic resinous products having a wax-like, i.e., hard, brittle, relatively non-greasy, texture, such as silicone waxes.

The oil portion of the anhydrous base preferably includes one or more cosmetically acceptable oils or oil-like emollients. Any cosmetically or pharmaceutically acceptable oil may be used in the wax base, the selection being made to some extent upon the desired viscosity of the final product. Examples of suitable oils or oil-like emollients can be found in the International Cosmetic Ingredient Handbook, CTFA, 1996, the contents of which are incorporated herein by reference. Useful materials include, but are not limited to, castor oil, coconut oil, corn oil, jojoba oil, cottonseed oil, soybean oil, walnut oil, wheat germ oil, sunflower seed oil, palm kernel oil, calendula oil, C10–18 triglycerides, lanolin and lanolin derivatives, illipe butter, shea butter; esters having the formula RCO—OR' wherein RCO represents a carboxylic acid radical and OR' represents an alcohol residue, such as isodecyl neopentanoate, tridecyl octanoate, cetyl palmitate, cetyl octanoate, cetyl stearate, cetyl myristate, isopropyl palmitate, isopropyl myristate, polyglyceryl-2-isostearate, neopentyl glycol distearate, isodecyl oleate, decyl isostearate, diisopropyl sebacate, PEG-4 diheptanoate, dioctyl malate, and isohexyl neopentanoate; fatty alcohols, such as lanolin alcohol or oleyl alcohol; and silicone oils, such as cyclomethicone, dimethicone, cetyl dimethicone, lauryl trimethicone, and dimethiconol. The oil component comprises from at least about 30–80% of the anhydrous component, and from about 20–70%, more preferably about 50–70%, of the total weight of the wax-based product. In a particularly preferred embodiment, at least half of the oil component is made up of one or more polar oils. Preferably, at least about 25%, more preferably at least about 30%, most preferably at least about 40–50%, and up to 70%, of the wax based product as a whole is made up of one or more polar oils, which are more compatible with water and aid in maintaining the stability of the product. A polar oil is a non-hydrocarbon oil, particularly one which contains alcohol residues, or an ester or triglyceride component.

Examples of useful polar oils include but are not limited to vegetable oils, such as jojoba oil, shea butter, almond oil, peach kernel oil, sesame seed oil and the like; and fatty esters, such as neopentyl glycol dicaprate, or polyglyceryl-2-diisostearate. The oil component can comprise one or any combination of these polar oils To prepare an emulsion of the anhydrous base with an aqueous component, an emulsifier having an HLB of 7 or less is employed. From about 0.5–5%, more preferably from about 0.5–3%, of the wax-based product as a whole is emulsifier, which may be a part of the anhydrous base, or incorporated separately. In a preferred embodiment the emulsifier has an HLB of from about 5–7. It is particularly preferred that a non-ionic emulsifier be employed. Examples of such emulsifiers can be found in McCutcheons Emulsifiers and Detergents, the contents of which are incorporated herein by reference. Particularly preferred emulsifiers are sorbitan sesquioleate, and PEG-7 hydrogenated castor oil. Although the emulsifier can be used in an amount of up to about 5% of the total weight of the composition, it has been surprisingly found that as little as 1–2% provides a very stable water-in-oil emulsion. This is particularly unexpected when a large quantity of water, e.g., 5% or more, is being employed, and provides a particular advantage in that the potential for irritation is significantly reduced by the presence of very low level of emulsifier in the product.

The wax base may also comprise other optional components, depending on the intended end use and form of the final product. For example, for a colored lipstick product, one or more pigment compounds will be added. The pigment may be any that are cosmetically acceptable for use in a lip product. These include both inorganic and organic compounds, for example, inorganic metallic oxides, mica, bismuth oxychloride, or D&C and FD&C dyes. If used, the pigment is generally employed at a level of from about 0.5–15%.

The vesicular component, when prepared as described above, is also added to the wax base, in an amount sufficient to provide about 0.5–30% water in the final formulation, preferably about 1–10%, more preferably about 4–8%, water. It will be understood that a portion of the water incorporated into the wax base with the vesicular component is not encapsulated, but is instead part of the continuous aqueous phase in which the vesicles are suspended. Alternately, in place of the vesicles, water alone can be added directly to the wax base, in an amount of from about 0.5–20% of the total formulation.

The final product may also benefit from the addition of a small quantity e.g., from about 0.01–1%, of a high melting point polyethylene to the formulation. The addition of this material aids in water retention, making the base less porous, and also aids in dispersion of the water component throughout the product. Polyethylene also can add to the structural integrity of a solid stick product, aiding in preventing breakage.

Biologically active materials which are lipid compatible can also be added directly to the wax base. These actives may be any which are appropriate for the intended end use of the product and the target area to which the product is to be applied; for example, the base can contain lipophilic treatment or conditioning materials such as Vitamin E and derivatives, Vitamin A and derivatives, lipophilic antioxidants, emollients such as petrolatum or dimethicone, long-chain alpha hydroxy acids, ceramides, or skin lipids to enhance barrier function. Those skilled in the art will recognize that for either the lipid or the aqueous phase, other actives for topical application can be chosen from analgesics, anesthetics, anti-acne agents, antibacterials, antiyeast agents, antifungal agents, antiviral agents, antidandruff agents, antidermatitis agents, antipruritic agents, antiemetics, antimotion sickness agents, anti-inflammatory agents, antihyperkeratolytic agents, anti-dry skin agents, antiperspirants, antipsoriatic agents, antiseborrheic agents, hair conditioners and hair treatment agents, antiaging agents, antiwrinkle agents, antiasthmatic agents and bronchodilators, sunscreen agents, antihistamine agents, skin lightening agents, depigmenting agents, wound-healing agents, vitamins, corticosteroids, tanning agents, or hormones. It is a routine matter to determine into which phase of the wax-based product the active is most conveniently incorporated.

Preservatives may also be employed, in an amount of from 0.01–5%, preferably from 0.01–1%, of the formula weight. Examples of suitable preservatives are BHA, BHT, propyl paraben, or methyl paraben.

It will be understood that, although the product of the present invention has been exemplified in the form of a lipstick, the formulation can be applied not to only lipsticks in a cosmetic sense, but to any wax-based product intended for topical or parenteral application of treatment or conditioning materials. Additional examples include, but are not limited to, a stick product to be used as a lip balm, for application of pharmaceutical products to the lip area, a pot-contained lip product, a deodorant stick, or any waxy product which is intended to deliver cosmetic or pharmaceutical actives. Additional embodiments of the present invention will be readily apparent to those skilled in the art. The invention is further illustrated by the following non-limiting examples.

EXAMPLES

Example 1

The following describes the preparation of a lamellar vesicle for use in the lip product

| MATERIAL | WEIGHT % |
|---|---|
| Glyceryl distearate | 5.0 |
| Stearyl alcohol | 0.4 |
| Steareth-10 | 3.0 |
| PEG-soy sterol | 2.0 |
| C40–C60 pareth-3 | 3.0 |
| Polysorbate 80 | 2.0 |
| Castor Oil | 20.0 |
| Deionized water | QS |
| Disodium EDTA | 0.1 |

All ingredients except the deionized water and EDTA are combined in a jacketed support kettle to form the lipophilic phase, heated to 95–100° C. under propeller agitation, and mixed until clear. The remaining ingredients are combined and heated to about 70–75° C. The lipophilic phase is forcibly injected, by way of a three-way stopcock, into the aqueous phase in a 25 ml syringe. The mixture is then forced into a second syringe at a flow-rate of $8-12 \times 10^2$ cm/sec through a 1 mm orifice, and then continuously driven between the two syringes for about two minutes, resulting in a milky suspension containing the lipid vesicles.

Example 2

The following formulation shows a solid lip product prepared in accordance with the present invention:

| MATERIAL | WEIGHT % |
| --- | --- |
| Phase 1 | |
| Polyethylene | 0.25 |
| paraffin | 1.50 |
| ceresin | 1.50 |
| neopentyl glycol dicaprate | 0.50 |
| polyglyceryl-2-triisostearate | 0.50 |
| Phase 2 | |
| refined jojoba oil | 10.00 |
| shea butter | 4.00 |
| candelilla wax | 1.00 |
| Phase 3 | |
| castor oil | 28.50 |
| carnauba wax | 1.50 |
| candelilla wax | 2.50 |
| ozokerite | 1.75 |
| beeswax | 2.50 |
| oleyl oleate | 5.00 |
| Polydecene | 1.50 |
| sorbitan sesquioleate | 1.20 |
| isodecyl neopentanoate | 0.25 |
| Phase 4 | |
| BHT | 0.20 |
| propyl paraben | 0.05 |
| Vitamin E | 0.15 |
| Phase 5 | |
| pigment | 11.00 |
| castor oil | 17.00 |
| Phase 6 | |
| multilamellar vesicles (as prepared in Example 1) | 8.15 |

Phase 1 materials are combined, and heated to 90° C. under 150–200 RPM mixer. The components are mixed until they are completely dissolved and the phase is clear and homogeneous. Once this is achieved, the phase is cooled to 850° C.

Phase 2 materials are added to Phase 1 at 85° C. under continuous 150–200 RPM mixer agitation, until the mixture is clear and homogeneous.

Phase 3 materials are added to the Phase 1 and 2 mixture at 85° C. under continuous agitation until the phase 3 materials are dissolved and the mixture is homogeneous.

Phase 4 materials are added to the already combined phases at 85° C. and mixed until the mixture is homogeneous. While maintaining the same temperature, the sequence 5 materials are combined with the mixture and mixed until the mixture is uniform. The phase 6 materials are added very slowly and carefully to the existing mixture. Mixing is continued at 200–250 RPM until all air bubbles disappear, then mixing is slowed down to 100–150 RPM. When the batch is completely uniform, it is cooled to 80° C., then mixed for another 10–15 minutes. The product is then poured into a mold at 80° C.

What we claim is:

1. A wax-based composition comprising at least about 0.5–30% water in a water-in-oil emulsion, wherein water is encapsulated in a lamellar lipid vesicle capable of withstanding wax melting point temperatures.

2. The composition of claim 1 wherein the vesicle comprises at least one high-melting point polyoxyethylene fatty ether.

3. The composition of claim 2 wherein the ether has a melting point of at least about 80° C.

4. The composition of claim 2 wherein the ether has a melting point of at least about 90° C.

5. The composition of claim 2 wherein the ether has a melting point of at least about 100° C.

6. The composition of claim 2 wherein the ether has a chain length of at least C20.

7. The composition of claim 2 wherein the ether has a chain length of at least C40.

8. The composition of claim 1 wherein the water-in-oil emulsion comprises greater than 5 to about 30% by weight of one or more waxes.

9. The composition of claim 8 which comprises an emulsifier having an HLB of about 7 or less.

10. The composition of claim 9 wherein the emulsifier has an HLB of from about 5 to about 7.

11. The composition of claim 10 wherein the emulsifier is nonionic.

12. The composition of claim 11 wherein the emulsifier is sorbitan sesquioleate.

13. The composition of claim 8 wherein the emulsifier is present in an amount of from about 1–2%.

14. The composition of claim 8 which comprises from about 20–70% of one or more oils.

15. The composition of claim 14 which comprises at least about 50% of one or more polar oils.

16. The composition of claim 1 in which the vesicle also comprises at least one water soluble active component.

17. An anhydrous lipstick base comprising from at least l10–40% waxes, from at least 30–80% oils, and an emulsifier, wherein at least 50% of the oil comprises one or more polar oils.

18. The base of claim 17, wherein the polar oil is a vegetable oil or a fatty ester.

19. The base of claim 17, wherein the emulsifier is a non-ionic emulsifier having an HLB of 7 or less.

20. The base of claim 17, wherein the emulsifier is present in an amount of from about 2–10%.

21. A cosmetic or pharmaceutical wax-based composition which is a water-in-oil emulsion, the emulsion comprising at least about 50% polar oils, from about 10–30% waxes, from about 0.5–5% emulsifier, and about 0.5–30% water.

22. A cosmetic or pharmaceutical composition for application to the lips comprising, in a water-in oil emulsion, from about 0.5–30% water, wherein water is encapsulated in a lamellar lipid vesicle which comprises at least one high-melting point polyoxyethylene fatty ether, and from 10–30% waxes, from 40–70% oils, and from 0.5–5% emulsifier, wherein at least about 50% of the composition as a whole comprises one or more polar oils selected from the group consisting of vegetable oils, triglycerides, fatty esters, or mixtures thereof.

23. The composition of claim 22, wherein the ether has a melting point of from at least about 80° C. to at least about 100° C.

24. The composition of claim 22 wherein the ether has a chain in length of at least C20.

25. The composition of claim 23 wherein the ether is C40–C60 pareth-3.

26. The composition of claim 22 wherein the emulsifier is a non-ionic emulsifier having an HLB of 7 or less, and is present in an. amount of from about 1–2% by weight of the total composition.

27. The composition of claim 26 wherein the emulsifier is sorbitan sesquioleate.

28. The composition of claim 22 which also comprises from 0.01–1% polyethylene.

29. The composition of claim 22 wherein the vesicle comprises at least one water soluble active.

30. The composition of claim 22 which comprises from about 5–10% water, from about 10–20% waxes, from about 50–70% polar oils, from about 1–2% emulsifier, from about 0.1–1% polyethylene, and to at least one water soluble active.

31. A method of delivering water soluble actives to the skin comprising applying to the skin the composition of claim 1 into which the actives have been incorporated.

* * * * *

UNITED STATES PATENT AND TRADEMARK OFFICE
CERTIFICATE OF CORRECTION

PATENT NO. : 6,280,753 B1
DATED : August 28, 2001
INVENTOR(S) : Chung et al.

It is certified that error appears in the above-identified patent and that said Letters Patent is hereby corrected as shown below:

Title page,
Item [74], please replace "L" with -- LLP --;

Column 8, claim 17,
Line 2, thereof, please replace "least110-40%" with -- least 10-40% --;

Column 8, claim 24,
Line 2, thereof, "in" should be deleted; and

Column 8, claim 26,
Line 3, thereof, please replace "an." with -- an --.

Signed and Sealed this

Twelfth Day of March, 2002

Attest:

Attesting Officer

JAMES E. ROGAN
Director of the United States Patent and Trademark Office